United States Patent [19]

Gowdy, Jr.

[11] Patent Number: 4,796,986

[45] Date of Patent: Jan. 10, 1989

[54] COMBINATION SAFETY GLASSES

[76] Inventor: Wilford B. Gowdy, Jr., Rt. 1, Box 157, Cades, S.C. 29518

[21] Appl. No.: 167,724

[22] Filed: Mar. 14, 1988

[51] Int. Cl.$^4$ ................................................ G02C 7/08
[52] U.S. Cl. ........................................ 351/57; 351/149
[58] Field of Search ................ 351/154, 149, 47, 57; 2/442, 443, 444

[56] References Cited

U.S. PATENT DOCUMENTS

| | | | |
|---|---|---|---|
| 1,923,567 | 8/1933 | Baker | 351/57 |
| 3,425,774 | 2/1969 | Lindblom | 351/149 |

FOREIGN PATENT DOCUMENTS 610452  4/1949  United Kingdom .................. 351/57

Primary Examiner—Rodney B. Bovernick
Assistant Examiner—P. M. Dzierzynski
Attorney, Agent, or Firm—Walter F. Wessendorf, Jr.

[57] ABSTRACT

Combination safety glasses having frame lens openings fitted with non-correcting safety lenses. Raised portions from the rear of said frame lens openings are of integral, one-piece construction therewith. The raised portions have guide recesses that receive and dispose correcting lenses in parallel relationship with the non-correcting lenses. The correcting lenses are of the full magnifier, full prescription, full bifocal or half prescription type. Opposite ends of the raised portions have nasal-side detents and spring-biased, temporal-side locking detents. The nasal-side detents are of integral one-piece construction with the raised portions, while the temporal-side locking detents are resilient and have spring biasing actions thereby rendering the locking detents spring-biased. The nasal-side detents engage the correcting lenses. The locking detents are cammed outwardly by engagement with the correcting lenses and are thereby spring-biased, and thereafter the locking detents are relieved to return to removable locking engagement with the correcting lenses.

1 Claim, 1 Drawing Sheet

COMBINATION SAFETY GLASSES

BACKGROUND OF THE INVENTION

1. Technical Field

This invention relates to combination safety glasses for use in detachably mounting, in locked relationship, full magnifier lenses, full prescription lenses, full bifocal lenses or half prescription lenses in parallel relationship with the non-correcting lenses conventionally fitted with the frame lens openings of the safety glasses.

2. Background

The problem in the art to which this invention appertains when safety glasses are used by a person who needs to wear correcting lenses of the full magnifier, full prescription, full bifocal or half prescription type is the need for safety glasses which permit correcting lenses of the full magnifier, full prescription, full bifocal or half prescription type to be detachably mounted therewith, in locked relationship, to provide for the vision needs of such person wearing safety glasses.

SUMMARY OF THE INVENTION

The object of this invention is to contribute to the solution of the discussed problem of the art by providing combination safety glasses which, on the one hand, retains the protective feature of conventionally fitted non-correcting lenses, but, on the other hand, provides for a person's vision needs by detachably mounting, in locked relationship, correcting lenses of the full magnifier, full prescription, full bifocal or half prescription type in parallel relationship with non-correcting lenses fitted with the frame lens openings of the safety glasses.

BRIEF DESCRIPTION OF THE DRAWINGS

This object and other objects of the invention should be discerned and appreciated from the description of the preferred embodiment, taken in conjunction with the drawings, wherein like reference numerals refer to similar parts throughout the several views, in which.

DESCRIPTION OF THE PREFERRED EMBODIMENT

Figure 1:
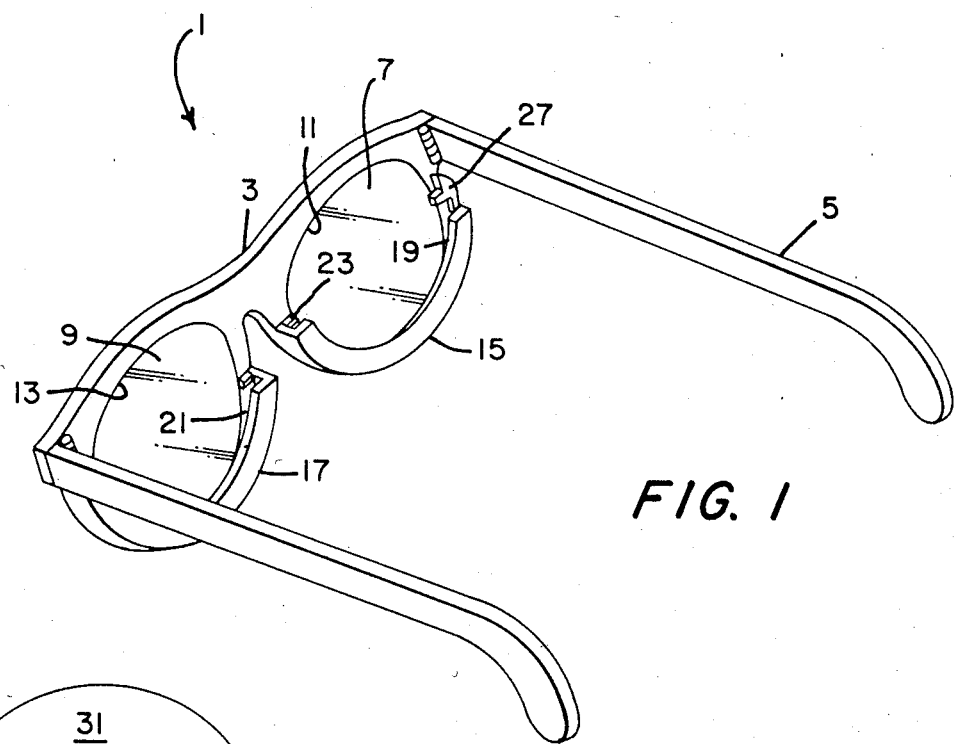
FIG. 1 is a perspective view of the invention.

In FIG. 1 of the drawings, reference numeral 1 generally refers to the combination safety glasses having a frame 3 and pivotable temples 5. Frame 3 and temples 5 are of plastic or other suitable material. Non-correcting right and left safety lenses 7 and 9 are conventionally fitted with the right and left lens openings 11 and 13 of frame 3. The rear of right and left lens openings 11 and 13 have, integral therewith and of one-piece construction, right and left raised portions 15 and 17 along the bottom-half portions of the lens openings 11 and 13. Formed with raised portions 15 and 17 are respective guide recesses 19 and 21. Raised portions 15 and 17 have formed therewith, of integral one-piece construction, and at one end of said raised portions 15 and 17, right and left nasal-side detents 23 and 25, respectively, while the other ends of raised portions 15 and 17 terminate in respective spring-biased, temporal-side locking detents 27 and 29. The locking detents 27 and 29 are not of integral one-piece construction with the plastic material of the lens openings 11 and 13 and, hence, have spring biasing locking actions for reason of the resiliency of their terminal portions.

Figure 2:
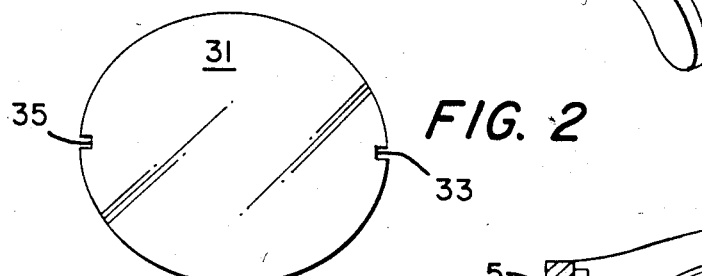
FIG. 2 is a view of a left, full magnifier or prescription lens.
Figure 3:
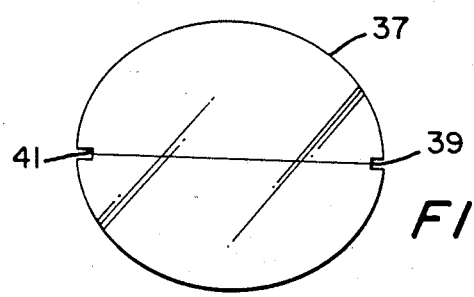
FIG. 3 is a view of a left, bifocal prescription lens.
Figure 4:
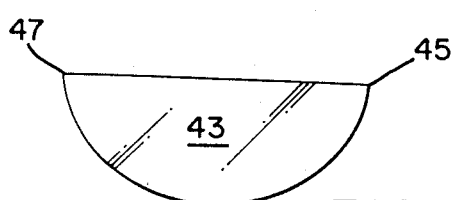
FIG. 4 is a view of a left, half prescription lens.
Figure 5:
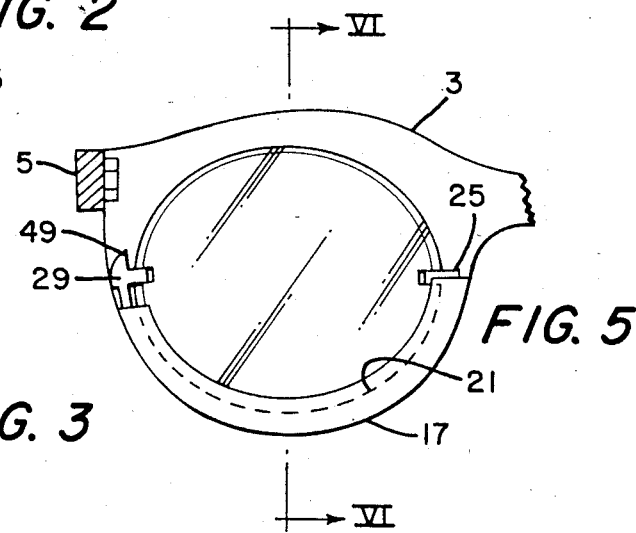
FIG. 5 is a view of the left half of the invention, as viewed from the rear; and, FIG. 6 is a sectional view taken in the direction of the arrows VI—VI in FIG. 5.
Figure 6:
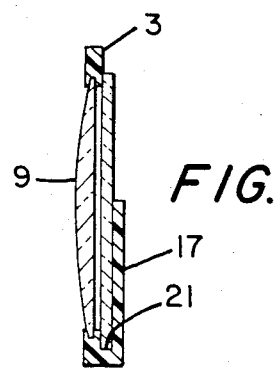

The combination safety glasses 1 detachably mounts, in locked relationship, correcting lenses of the full magnifier, full prescription, full bifocal or half prescription type. FIG. 2 shows a left, full lens 31 which may be of the magnifier or prescription type. The alternative language is employed because the drawing figure for either type would be the same. Lens 31 has a nasal-side detent guide notch 33 and a temporal-side detent locking notch 35. FIG. 3 shows a left, full prescription lens 37 of the bifocal type having a nasal-side detent guide notch 39 and a temporal-side detent locking notch 41. FIG. 4 shows a left, half prescription lens 43. Lenses 31, 37 and 43 are detachably mounted with respect to the left raised portion 17.

In detachably mounting left lens 31, same is appropriately manipulated such that left nasal-side detent 25 is engaged with left lens detent nasal-side guide notch 33. Then lens 31 is pushed downwardly and sufficiently with the result that the periphery or edge of lens 31 will engage left locking detent 29 and cam outwardly locking detent 29 to its left. When locking detent 29 is aligned with left lens locking notch 35, the inherently imposed spring bias on locking detent 29 will be relieved and locking detent 29 will return to its right to effect locking engagement with left lens detent locking notch 35, and the periphery or edge of lens 31 in common with left guide recess 21 will be completely received within recess 21, and lens 31 will be disposed in parallel relationship with left safety lens 9.

In detachably mounting left lens 37, same is appropriately manipulated such that left nasal-side detent 25 is engaged with left nasal-side guide detent notch 39. Then lens 37 is pushed downwardly and sufficiently with the result that the periphery of lens 37 will engage left locking detent 29 and cam outwardly locking detent 29 to its left. When locking detent 29 is aligned with left lens temporal-side detent locking notch 41, the inherently imposed spring bias on locking detent 29 will be relieved and locking detent 29 will return to its right to effect locking engagement with left lens detent locking notch 41, and the periphery of lens 37 in common with left guide recess 21 will be completely received within recess 21, and lens 37 will be disposed in parallel relationship with left safety lens 9.

In detachably mounting left, half prescription lens 43, the right pointed portion 45 is inserted under and abutting left nasal-side detent 25. Then lens 43 is pushed downwardly and sufficiently with the result that the periphery or edge of lens 43 will engage left locking detent 29 and cam outwardly detent 29 to its left, imposing spring-bias on detent 29, which will be relieved when the left pointed portion 47 of lens 43 is disposed below detent 29. Thereupon, detent 29 will spring back to its right to effect locking engagement with left pointed portion 47 and the periphery of lens 43 in common with left guide recess 21 will be completely received within recess 21, and the lens 43 will be disposed in parallel relationship with safety lens 9.

To remove lenses 31, 37 or 43, the finger tab 49 of left locking detent 29 is appropriately manipulated to dispose same to its left free from engagement with such lens 31, 37 or 43, and lens 31, 37 or 43 is simply removed by lifting same out.

The right lenses corresponding to left lenses 31, 37 and 43 are not shown but their configurations would be appropriate for parallel emplacement with respect to the right safety lens 7; and their nasal-side detent guide and temporal-side locking notches would be similar to the detent nasal-side guide and temporal-side locking notches 33 and 35 of lens 31, and 39 and 41 of lens 37, but oriented in the opposite directions. Moreover, the detachable mounting and removal of the right correcting lenses of the full magnifier, full prescription, full bifocal and half prescription type via right nasal-side detent 23 and right spring-biased, temporal-side locking detent 27 would be similar to the operation described with reference to left nasal-side detent 25 and left temporal-side locking detent 29.

Having thusly described my invention, I claim:

1. Combination safety lenses for detachably mounting, in locked relationship, correcting lenses of the full magnifier, full prescription or full bifocal type to provide for the vision needs of a person wearing safety glasses; said combination safety glasses comprising a frame having lens openings, said lens openings fitting non-correcting safety lenses therein, said lens openings having bottom half portions, said lens openings having, along their said bottom half portions, rearwardly projecting raised portions integral with said lens openings and of one-piece construction, said lens openings and rearwardly projecting portions being in parallel relationship, each of said lens openings and projecting portions forming a continuous channel, said channel defining a guide recess receiving therein and disposing thereby said correcting lens in parallel relationship with its corresponding non-correcting safety lens, each of said raised projecting portions having a nasal-side end and a temporal-side end, said nasal-side end having a nasal-side detent of integral, one-piece construction with its said nasal-side end, said temporal-side end having a temporal-side detent, said temporal-side detent being resilient and having a spring biasing locking action, each of said correcting lenses having a periphery, said periphery having cut therein a nasal-side guide notch and an opposite temporal-side locking notch, said nasal-side detents engaging, in guiding relationship, said nasal-side guide notches, said temporal-side detents cooperating with and engaging said temporal-side locking notches to automatically effect spring-biased removable locking engagements with said temporal-side locking notches.

* * * * *